US009398890B2

(12) United States Patent  
Dong et al.

(10) Patent No.: US 9,398,890 B2
(45) Date of Patent: Jul. 26, 2016

(54) GEOMETRY CALIBRATION ALGORITHM FOR LARGE FLAT MODULE DETECTOR CT SCANNER

(71) Applicant: GE MEDICAL SYSTEMS GLOBAL TECHNOLOGY COMPANY, LLC, Waukesha, WI (US)

(72) Inventors: Jiaqin Dong, Beijing (CN); Shuo Li, Beijing (CN); Jun Li, Sichuan (CN); Ximiao Cao, Beijing (CN); Bin Wang, Sichaun (CN)

(73) Assignee: GE MEDICAL SYSTEMS GLOBAL TECHNOLOGY COMPANY, LLC, Waukesha, WI (US)

( * ) Notice: Subject to any disclaimer, the term of this patent is extended or adjusted under 35 U.S.C. 154(b) by 239 days.

(21) Appl. No.: 14/168,088

(22) Filed: Jan. 30, 2014

(65) Prior Publication Data
US 2014/0211925 A1 Jul. 31, 2014

(30) Foreign Application Priority Data

Jan. 31, 2013 (CN) .......................... 2013 1 0037546

(51) Int. Cl.
*A61B 6/03* (2006.01)
*A61B 6/00* (2006.01)

(52) U.S. Cl.
CPC .................. *A61B 6/585* (2013.01); *A61B 6/032* (2013.01); *A61B 6/583* (2013.01)

(58) Field of Classification Search
CPC .......... A61B 6/03; A61B 6/032; A61B 6/582; A61B 6/583; A61B 6/584; A61B 6/585; A61B 6/4429; A61B 6/4435; A61B 6/4441; G01N 23/04
See application file for complete search history.

(56) References Cited

U.S. PATENT DOCUMENTS

| | | | | |
|---|---|---|---|---|
| 5,214,578 A * | 5/1993 | Cornuejols | ........... | G06T 11/005 378/18 |
| 5,822,396 A | 10/1998 | Navab | | |
| 7,950,849 B2 | 5/2011 | Claus et al. | | |
| 8,249,213 B2 * | 8/2012 | Noordhoek | ............ | A61B 6/583 378/11 |
| 2007/0122020 A1 * | 5/2007 | Claus | ..................... | A61B 6/583 382/131 |
| 2007/0290125 A1 * | 12/2007 | Wang | ................... | G01T 1/1648 250/252.1 |
| 2008/0116386 A1 * | 5/2008 | Wagenaar | ............... | G01T 1/249 250/370.09 |
| 2008/0240365 A1 * | 10/2008 | Holt | ........................ | G01D 18/00 378/207 |
| 2010/0195804 A1 * | 8/2010 | Dafni | ..................... | A61B 6/032 378/207 |
| 2011/0085645 A1 * | 4/2011 | Paidi | ...................... | A61B 6/584 378/207 |
| 2012/0076259 A1 * | 3/2012 | Holt | ......................... | A61B 6/03 378/18 |
| 2013/0039458 A1 * | 2/2013 | Ikhlef | ................... | G01T 1/2985 378/19 |

OTHER PUBLICATIONS

Yang et al, "A Geometric Calibration Method for Cone Beam CT Systems", Med Phys. Jun. 2006; 33 (6); 1695-1706.*
Kai Yang; A Geometric Calibration Method for Cone Beam CT Systems; Med. Phys. 2005 32 (4).
Cho Y; Accurate Technique for Complete Geometric Calibration of Cone-Beam Computed Tomography Systems; Med. Phys. Apr. 2006; 32 (4).

* cited by examiner

*Primary Examiner* — Robert Kim
*Assistant Examiner* — David E Smith
(74) *Attorney, Agent, or Firm* — GE Global Patent Operation (57) ABSTRACT

A method for geometric calibration of a CT scanner, including, for each row of at least one row of detector cells, establishing a complete geometric description of the CT scanner, including at least one unknown geometric parameter, establishing a description of a forward projection function using the complete geometric description, acquiring actual projection coordinates of a calibration phantom placed in a scanning field of view (SFOV) on a current row of detector cells and corresponding to a plurality of angles, acquiring calculated projection coordinates of the calibration phantom on the current row of detector cells and corresponding to the plurality of angles using the description of the forward projection function, and acquiring a calibrated value for the at least one unknown geometric parameter by evaluating the at least one unknown geometric parameter based on the acquired actual projection coordinates and calculated projection coordinates via a nonlinear least square fitting algorithm.

16 Claims, 8 Drawing Sheets

GEOMETRY CALIBRATION ALGORITHM FOR LARGE FLAT MODULE DETECTOR CT SCANNER

TECHNICAL FIELD

The present disclosure relates to the field of computer tomography (CT), and in particular, to a method and an apparatus for geometric calibration of a CT scanner.

BACKGROUND ART

To save on the cost of detectors in a CT scanner, a large flat module detector has been introduced in the CT scanner. This large flat module detector has a plurality of flat modules, each module having a plurality of packs, each pack having a plurality of conventional detector cells. Compared to the traditional 3rd generation curved detector architecture, this large flat module detector is much larger, and is also different in many other ways. For example, in a large flat module detector, there exist air gaps between adjacent modules and between adjacent packs, while the traditional 3rd generation curved detector architecture contains no such air gaps.

Due to the actual manufacture and installation techniques of detectors, coherence between the actual sizes of these air gaps and the designed size thereof can hardly be guaranteed. Typically, coherence between the actual sizes of air gaps between adjacent packs and the designed size thereof is relatively easy to achieve during manufacturing. Moreover, because packs in a same module can be installed parallel to each other, the sizes of air gaps between adjacent packs will not be subjected to large errors during the installation. However, since the modules in the detector are typically installed obliquely at a certain angle relative to each other, stochastic errors will be introduced in the sizes of air gaps between adjacent modules, such that the sizes of air gaps between adjacent modules may be different in the same detector, and among different systems.

Furthermore, for a large flat module detector, obliquely incident X-ray photons may affect the effective response positions of the detector cells at the module edges, such that the effective response positions thereof are not at the centers of the detector cells, thereby affecting the sizes of air gaps between adjacent modules.

Due to at least these factors, the sizes of air gaps between adjacent modules in the large flat module detector become immeasurable. However, accurate air gap sizes, particularly the sizes of air gaps between adjacent modules, are very important for image reconstruction with a high image quality. Any mismatch between data acquisition and image reconstruction resulting from incoherence between the actual sizes of air gaps between adjacent modules and the designed size thereof may lead to severe ring artifacts in the reconstructed images.

For example, for a large flat module detector with a structure of 5 (the number of modules in the detector)×4 (the number of packs in each module)×34 (the number of detector cells in each pack), it is required that the size of air gaps between adjacent packs is 0.05 mm, and the size of air gaps between adjacent modules is 0.15 mm. In general, during the manufacture and installation of the detector, the errors introduced for the size of air gaps between adjacent packs are less than ±0.02 mm, while the errors introduced for the size of air gaps between adjacent modules are less than ±0.15 mm. When the errors introduced for the size of air gaps between adjacent modules are greater than ±0.04 mm, ring artifacts will occur in the reconstructed images, which is undesirable.

On the other hand, after the detector is secured to the gantry, its position cannot be adjusted. However, considering the precision of the mounting, the position of the detector may not correspond exactly to the desired position, which will affect the ISO channel. In other words, the actual ISO channel may not be the desired ISO channel. If an inaccurate ISO channel is adopted in the image reconstruction process, the Modulation Transfer Function (MTF) will be degraded. More seriously, double shadow artifacts may appear in the reconstructed images.

Considering that the abovementioned geometric parameters (e.g., the sizes of air gaps between adjacent modules, and the ISO channel) are immeasurable but critical to fulfill a high-quality reconstructed image, there is needed a method and apparatus for geometric calibration of a CT scanner.

SUMMARY OF THE INVENTION

In order to solve the above mentioned problem, the present disclosure provides a simple and effective method and apparatus for geometric calibration of a CT scanner including a large flat module detector, whereby accurate sizes of air gaps between adjacent modules, an accurate ISO channel, and an improved MTF can be obtained.

The present disclosure provides a method for geometric calibration of a CT scanner having at least one row of detector cells, the method including executing the following for each row of said at least one row of detector cells: establishing a complete geometric description of the CT scanner, said complete geometric description including at least one unknown geometric parameter; establishing a description of a forward projection function using said complete geometric description; acquiring actual projection coordinates of a calibration phantom placed in a scanning field of view (SFOV) on a current row of detector cells and corresponding to a plurality of angles; acquiring calculated projection coordinates of the calibration phantom on the current row of detector cells and corresponding to the plurality of angles using the description of said forward projection function; and acquiring a calibrated value for said at least one unknown geometric parameter by evaluating said at least one unknown geometric parameter based on the acquired actual projection coordinates and calculated projection coordinates via a nonlinear least square fitting algorithm.

In the method according to one or more embodiments of the present invention, the current row of detector cells has a structure of n×q×r, where n denotes the number of modules, q denotes the number of packs in each module, and r denotes the number of detector cells in each pack.

In the method according to one or more embodiments of the present invention, said at least one unknown geometric parameter includes sizes of (n−1) air gaps between adjacent modules, and one ISO channel offset.

In the method according to one or more embodiments of the present invention, the forward projection function is described as follows:

$$X_{P\beta} = P_\beta(x, y, S);$$

wherein $X_{P\beta}$ denotes a calculated projection coordinate of the calibration phantom on the current row of detector cells and corresponding to a forward projection angle $\beta$, x and y are coordinates of the calibration phantom, S is a set including said at least one unknown geometric parameter, and P is a description of the forward projection function.

In the method according to one or more embodiments of the present invention, said calibrated value acquiring step includes an objective function minimizing step for minimizing the following objective function by evaluating said at least one unknown geometric parameter via said nonlinear least square fitting algorithm:

$$F=\Sigma_{i=1}^{m}(x'_p(\beta_i)-P_{\beta_i}(x,y,S))^2;$$

wherein F denotes the objective function, $\beta_i$ denotes a current scan angle; m represents the number of scan angles, $x'_p(\beta_i)$ represents an actual projection coordinate of the calibration phantom on the current row of detector cells and corresponding to the current scan angle, and $P_{\beta_i}(x, y, S)$ denotes a calculated projection coordinate of the calibration phantom on the current row of detector cells and corresponding to the current scan angle.

In the method according to one or more embodiments of the present invention, the actual projection coordinate of the calibration phantom on the current row of detector cells and corresponding to the current scan angle is the Gaussian center of projection data of the calibration phantom on the current row of detector cells and corresponding to the current scan angle.

In the method according to one or more embodiments of the present invention, the actual projection coordinates of the calibration phantom on the current row of detector cells and corresponding to said plurality of angles are obtained by an axial scan of the calibration phantom for said plurality of angles.

In the method according to one or more embodiments of the present invention, said nonlinear least square fitting algorithm includes the Powell optimization algorithm.

In the method according to one or more embodiments of the present invention, the calibration phantom is a pin having a length of 100 mm and a diameter of 2 mm.

In the method according to one or more embodiments of the present invention, the calibrated value for said at least one unknown geometric parameter is used for subsequent image reconstruction.

The present disclosure also provides an apparatus for geometric calibration of a CT scanner having at least one row of detector cells, said apparatus including: a geometric description establishing device for establishing a complete geometric description of the CT scanner, said complete geometric description including at least one unknown geometric parameter; a forward projection function establishing device for establishing a description of a forward projection function using said complete geometric description; an actual projection coordinate acquiring device for acquiring actual projection coordinates of a calibration phantom placed in a scanning field of view (SFOV) on a current row of detector cells and corresponding to a plurality of angles; a calculated projection coordinate acquiring device for acquiring calculated projection coordinates of the calibration phantom on the current row of detector cells and corresponding to the plurality of angles using the description of said forward projection function; and a calibrated value acquiring device for acquiring a calibrated value for said at least one unknown geometric parameter by evaluating said at least one unknown geometric parameter based on the acquired actual projection coordinates and calculated projection coordinates via a nonlinear least square fitting algorithm.

In the apparatus according to one or more embodiments of the present invention, the current row of detector cells has a structure of n×q×r, where n denotes the number of modules, q denotes the number of packs in each module, and r denotes the number of detector cells in each pack.

In the apparatus according to one or more embodiments of the present invention, said at least one unknown geometric parameter includes sizes of (n−1) air gaps between adjacent modules, and one ISO channel offset.

In the apparatus according to one or more embodiments of the present invention, the forward projection function is described as follows:

$$x_{p\beta}=P_\beta(x,y,S);$$

wherein $x_{p\beta}$ denotes a calculated projection coordinate of the calibration phantom on the current row of detector cells and corresponding to a forward projection angle $\beta$, x and y are coordinates of the calibration phantom; S is a set including said at least one unknown geometric parameter, and P is a description of the forward projection function.

In the apparatus according to one or more embodiments of the present invention, said calibrated value acquiring device includes an objective function minimizing device for minimizing the following objective function by evaluating said at least one unknown geometric parameter via said nonlinear least square fitting algorithm:

$$F=\Sigma_{i=1}^{m}(x'_p(\beta_i)-P_{\beta_i}(x,y,S))^2;$$

wherein F denotes the objective function, $\beta_i$ denotes a current scan angle; m represents the number of scan angles, $x'_p(\beta_i)$ represents an actual projection coordinate of the calibration phantom on the current row of detector cells and corresponding to the current scan angle, and $P_{\beta_i}(x,y,S)$ denotes a calculated projection coordinate of the calibration phantom on the current row of detector cells and corresponding to the current scan angle.

In the apparatus according to one or more embodiments of the present invention, the actual projection coordinate of the calibration phantom on the current row of detector cells and corresponding to the current scan angle is the Gaussian center of projection data of the calibration phantom on the current row of detector cells and corresponding to the current scan angle.

In the apparatus according to one or more embodiments of the present invention, the actual projection coordinates of the calibration phantom on the current row of detector cells and corresponding to said plurality of angles are obtained by an axial scan of the calibration phantom for said plurality of angles.

In the apparatus according to one or more embodiments of the present invention, said nonlinear least square fitting algorithm includes the Powell optimization algorithm.

In the apparatus according to one or more embodiments of the present invention, the calibration phantom is a pin having a length of 100 mm and a diameter of 2 mm.

In the apparatus according to one or more embodiments of the present invention, the calibrated value for said at least one unknown geometric parameter is used for subsequent image reconstruction.

The present disclosure further provides a CT scan system, including an apparatus for geometric calibration of a CT scanner having at least one row of detector cells. The apparatus including: a geometric description establishing device configured to establish a complete geometric description of the CT scanner, the complete geometric description including at least one unknown geometric parameter; a forward projection function establishing device configured to establish a description of a forward projection function using the complete geometric description; an actual projection coordinate acquiring device configured to acquire actual projection coordinates of a calibration phantom placed in a scanning field of view (SFOV) on a current row of detector cells and corresponding to a plurality of angles; a calculated projection coordinate acquiring device configured to acquire calculated projection coordinates of the calibration phantom on the current row of detector cells and corresponding to the plurality of angles using the description of the forward projection function; and a calibrated value acquiring device configured for acquire a calibrated value for the at least one unknown geometric parameter by evaluating the at least one unknown geometric parameter based on the acquired actual projection coordinates and calculated projection coordinates via a nonlinear least square fitting algorithm.

The method and apparatus provided by the present disclosure can accurately obtain the immeasurable geometric parameters for a CT scanner with a large flat module detector. Embodiments of the present invention ensure the feasibility of applying a low cost large flat module detector into a CT scanner. Embodiments of the present invention are easy to implement, the calibration phantom is very simple, the scan protocol is an ordinary axial scan, and the calculation is fast. Furthermore, the present invention can accurately acquire the sizes of air gaps between adjacent modules and the ISO channel, such that artifacts induced by inaccurate sizes of air gaps between adjacent modules and the inaccurate ISO channel can be completely eliminated, and the MTF improved.

BRIEF DESCRIPTION OF THE DRAWINGS

The present invention will be more apparent to those skilled in the art upon reading the following detailed description of embodiments with reference to the accompanying drawings, in which.

DETAILED DESCRIPTION OF THE INVENTION

Embodiments of the invention described herein are illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference numerals have been repeated among the figures to indicate corresponding or analogous elements. Reference in the specification to "one embodiment" or "an embodiment" of the invention means that a particular feature, structure, or characteristic described in connection with the embodiment is included in at least one embodiment of the invention. Thus, the appearances of the phrase "in one embodiment" in various places throughout the specification are not necessarily all referring to the same embodiment.

The present invention acquires accurate geometric parameters of a CT scanner by geometric calibration of the CT scanner after installation of the CT scanner. Typically, a complete geometric description of the CT scanner is set up before the geometric calibration, i.e., the CT scanner is fully described through geometric parameters of the CT scanner. Such geometric parameters may be divided into two categories: geometric parameters related to the X-ray source; and geometric parameters associated with the detector.

Geometric parameters related to the X-ray source may include, for example, the X-ray source coordinates, the distance between the X-ray source and the ISO, the distance between the X-ray source and the detector, etc.

Geometric parameters associated with the detector may include, for example, the size of the detector cell, the number of the detector cells, the ISO channel offset, etc. When the CT scanner has a large flat module detector, geometric parameters associated with the detector may further include, for example, the sizes of air gaps between adjacent modules, and the sizes of air gaps between adjacent packs.

Normally, geometric parameters related to the X-ray source can be accurately measured; and among the geometric parameters associated with the detector, the size and number of the detector cells can also be accurately known. However, geometric parameters such as the ISO channel offset, the sizes of air gaps between adjacent modules, and the sizes of air gaps between adjacent packs, are typically inaccurately measurable or immeasurable, due to errors introduced by the actual manufacture and installation techniques of the detector.

In order to obtain the actual values of such geometric parameters that are inaccurately measurable or immeasurable, the present invention places a calibration phantom in the SFOV, conducts an axial scan of this calibration phantom via a CT scanner to acquire actual projection coordinates of the calibration phantom on the current row of detector cells and corresponding to a plurality of angles, applies a forward projection function to this calibration phantom to acquire calculated projection coordinates of the calibration phantom on the current row of detector cells and corresponding to the plurality of angles, and evaluates such geometric parameters that are inaccurately measurable or immeasurable, based on the acquired actual and calculated projection coordinates for the plurality of angles via a nonlinear least square fitting algorithm so as to obtain values closest to the actual values. Values thus obtained are herein referred to as calibrated values.

In the following, the present invention will be described in detail via an example of a CT scanner having a large flat module detector with a structure of 5 (the number of modules in the detector)×4 (the number of packs in each module)×34 (the number of detector cells in each pack) in the x direction. Normally, such a large flat module detector used in a CT scanner may be arranged in 8 or 16 rows in the z direction, each row having 5×4×34 detector cells. To enhance precision, geometric calibration may be performed independently on each row of detector cells.

It should be noted that the present invention is not limited to CT scanners having a large flat module detector with a structure of 5×4×34 in the x direction, and CT scanners having a large flat module detector otherwise structured may also apply to the present invention. Besides, CT scanners with a curved detector architecture are also applicable to the present invention, where unknown geometric parameters, for example, the ISO channel offset, need evaluating.

Figure 1:
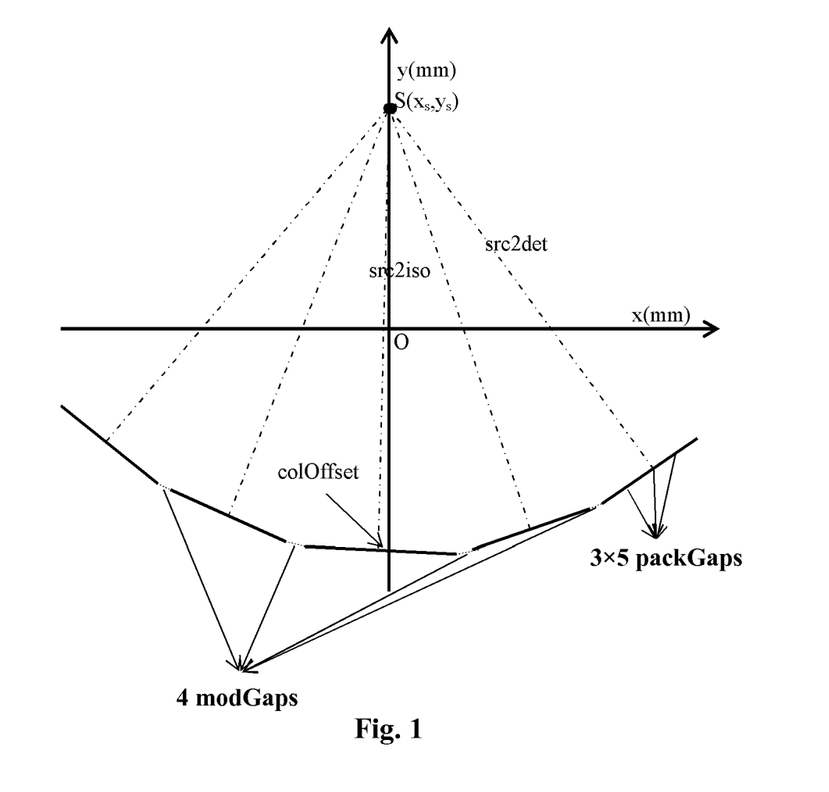
FIG. 1 is a schematic diagram showing a complete geometric description for a CT scanner having a large flat module detector according to one embodiment of the present invention.

FIG. 1 is a schematic diagram showing a complete geometric description for a CT scanner having a large flat module detector according to one embodiment of the present invention, wherein the CT scanner has a large flat module detector with a structure of 5×4×34 in the x direction, and $S(x_s, y_s)$ indicate the X-ray source coordinates. As shown in Table 1, the establishment of a complete geometric description for the CT scanner having a large flat module detector with a structure of 5×4×34 in the x direction requires geometric parameters of two categories: the X-ray source related geometric parameters and the detector related geometric parameters, which include a total of 26 geometric parameters.

small. Such small errors in the sizes of air gaps between adjacent packs will not lead to apparent artifacts in the reconstructed image in the presence of image noise. Therefore, the design value is typically adopted for the sizes of the air gaps between adjacent packs (i.e., 15 packGaps) during the image reconstruction process. Thus, the geometric calibration only relates to the following unknown geometric parameters: 1 colOffset, and 4 modGaps. In so doing, the number of the unknown geometric parameters is reduced from 20 to 5, thereby significantly decreasing the complexity of optimization and helping to obtain more reliable values of geometric parameters (namely, the ISO channel offset, and the sizes of air gaps between adjacent modules). These 5 unknown geometric parameters are crucial to a high quality reconstructed image, and need to be calibrated by experiments. As will be described in detail below, these 5 unknown geometric parameters will be evaluated via the nonlinear least square fitting algorithm.

Figure 2:
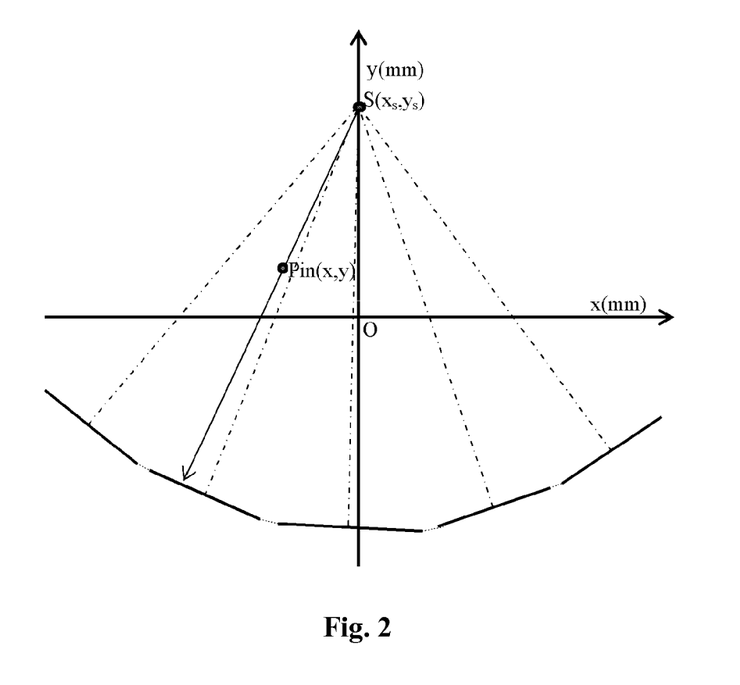
FIG. 2 is a schematic diagram illustrating a forward projection process for a CT scanner having a large flat module detector according to one embodiment of the present invention.

For a CT scanner with a complete geometric description established, any point in the SFOV can have a unique projection point on the detector through a forward projection function, as shown in FIG. 2. FIG. 2 is a schematic diagram illustrating a forward projection process for a CT scanner having a large flat module detector according to one embodiment of the present invention, wherein the CT scanner has a large flat module detector with a structure of 5×4×34 in the x direction, $S(x_s, y_s)$ denotes coordinates of the X-ray source, and Pin(x, y) denotes coordinates of the point to be scanned in the SFOV. The forward projection function corresponding to the CT scanner having a large flat module detector is very

TABLE 1

| Categories | Geometric parameters | Remarks on characteristics |
|---|---|---|
| X-ray source related | $x_s$: x-axis coordinate of the X-ray source (mm) | Accurately measurable, no drift |
| | $y_s$: y-axis coordinate of the X-ray source (mm) | Accurately measurable, no drift |
| | src2iso: distance from the X-ray source to the ISO (mm) | Accurately measurable |
| | src2det: distance from the X-ray source to the detector (mm) | Accurately measurable |
| Detector related | pixSize: size of the detector cell, i.e., distance between centers of adjacent detector cells (mm) | Accurately known |
| | numCell: number of detector cells in the current row | Accurately known |
| | colOffset: ISO channel offset of the current row of detector cells | Inaccurately measurable, but crucial to a high quality reconstructed image |
| | modGap: size of the air gap between adjacent modules of the current row of detector cells, with a total of 4 modGaps (mm) | Immeasurable, but crucial to a high quality reconstructed image |
| | packGap: size of the air gap between adjacent packs of the current row of detector cells, with a total of 3 × 5 packGaps (mm) | Immeasurable, and not crucial to a high quality reconstructed image |

Among the geometric parameters in Table 1, there are in fact 20 geometric parameters in total that are not accurately measurable or are immeasurable, i.e., 1 colOffset, 4 modGaps, and 15 packGaps. On the one hand, the designed value for the sizes of the air gaps between adjacent packs is only 0.05 mm, which is relatively small compared to the size of the detector cell and the distance between the X-ray source and the detector; on the other hand, the errors for the sizes of air gaps between adjacent packs incurred by the manufacture of the detector are normally ±0.02 mm, which are also very complicated, and may not have a simple analytical formula, but can be fully described by all the geometric parameters for setting up a complete geometric description of the CT scanner. For example, the forward projection process according to one embodiment of the present invention may be described as follows:

$$x_{P_\beta} = P_\beta(x, y, S) \qquad (1);$$

wherein $x_{P_\beta}$ denotes the calculated projection coordinate of a point in the SFOV on the current row of detector cells and corresponding to a forward projection angle β, x and y are coordinates of the point, S is a set of 5 unknown geometric parameters including the sizes of air gaps between adjacent modules (having a total number of 4) and the ISO channel offset (having a total number of 1), and P is a description of the forward projection function.

Equation (1) contains a total of 7 unknown parameters, which include: coordinates x and y of said point, and 5 geometric parameters to be calibrated, namely, the sizes of air gaps between adjacent modules (having a total number of 4) and the ISO channel offset (having a total number of 1).

Figure 3:
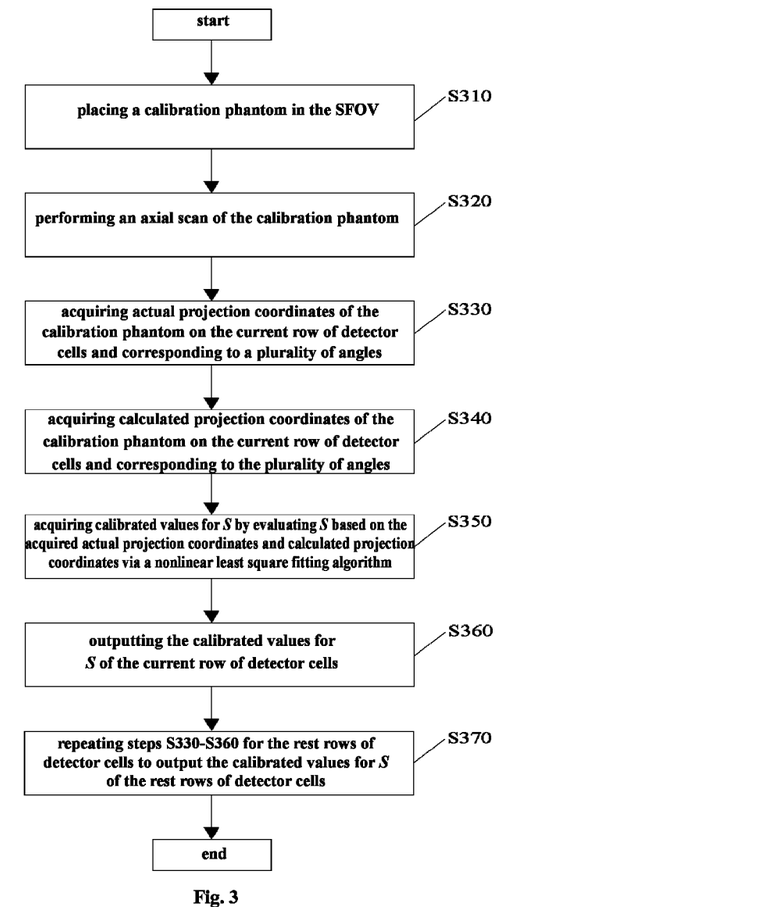
FIG. 3 is a flow chart showing a method for geometric calibration of a CT scanner having a large flat module detector according to one embodiment of the present invention.

FIG. 3 is a flow chart showing a method for geometric calibration of a CT scanner having a large flat module detector according to one embodiment of the present invention, wherein the CT scanner has a large flat module detector with a structure of 5×4×34 in the x direction.

At step S310, a calibration phantom of a suitable size is placed where appropriate in the SFOV, to ensure at least coverage of the air gaps between all adjacent modules of the current row of detector cells and ensure adequate equations for optimization. In one embodiment according to the present invention, a pin having a length of 100 mm and a diameter of 2 mm may serve as a calibration phantom and be placed about 200 mm off the SFOV center, so as to cover the air gaps between adjacent modules of all rows of detector cells.

At step S320, the CT scanner performs an axial scan of the calibration phantom for a plurality of angles, thereby obtaining projection images of the calibration phantom corresponding to the plurality of angles. In principle, S can be evaluated based on axial scan data acquisition for 7 angles. However, to achieve a high accuracy, in one embodiment according to the present invention, the CT scanner performs a complete axial scan of the calibration phantom. For example, it scans for one cycle in one second, thus producing 984 projection images, i.e., obtaining projection images of the calibration phantom corresponding to 984 angles.

Figure 4:
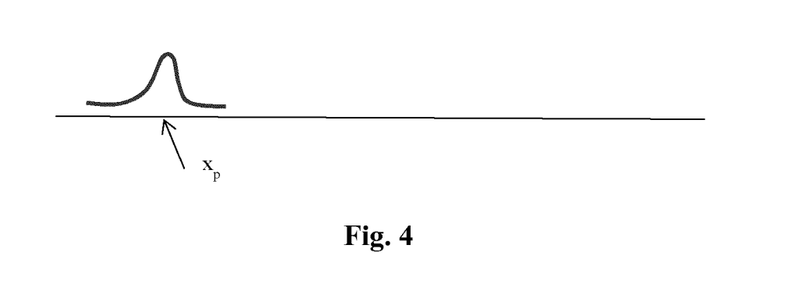
FIG. 4 shows a Gaussian center of projection data of the calibration phantom on the current row of detector cells and corresponding to the current scan angle according to one embodiment of the present invention.

At step S330, projection data of the calibration phantom on the current row of detector cells and corresponding to each angle are extracted from the obtained projection images of the calibration phantom corresponding to the plurality of angles, and the Gaussian center (i.e., the position of the detector cell corresponding to the maximum attenuation in the response curve) of the projection data of the calibration phantom on the current row of detector cells and corresponding to each angle is calculated, which serves as the actual projection coordinate of the calibration phantom on the current row of detector cells and corresponding to that angle, as shown by $x_p$ in FIG. 4.

At step S340, the forward projection function is applied to the calibration phantom to acquire calculated projection coordinates of the calibration phantom on the current row of detector cells and corresponding to the plurality of angles.

At step S350, the following objective function is optimized based on the actual and calculated projection coordinates via the nonlinear least square fitting algorithm, thereby acquiring calibrated values for x, y, and S corresponding to the current row of detector cells, which lead to the minimum value of the following objective function:

$$F=\Sigma_{i=1}^{m}(x'_p(\beta_i)-P_{\beta_i}(x,y,S))^2 \qquad (2);$$

wherein F denotes the objective function, $\beta_i$ denotes the current scan angle; m denotes the number of scan angles, $x'_p(\beta_i)$ denotes the actual projection coordinate of the calibration phantom on the current row of detector cells and corresponding the current scan angle, and $P_{\beta_i}(x, y, S)$ denotes the calculated projection coordinate of the calibration phantom on the current row of detector cells and corresponding the current scan angle. In one embodiment according to the present invention, the Powell optimization algorithm is utilized to optimize the following objective function:

$$F=\Sigma_{i=1}^{984}(x'_p(\beta_i)-P_{\beta_i}(x,y,S))^2 \qquad (3).$$

The optimization process will be further elaborated below.

At step S360, the calibrated values for S of the current row of detector cells are outputted.

At step S370, steps S330-S360 are repeated for the rest rows of detector cells, thereby outputting the calibrated values for S of the rest rows of detector cells.

The outputted calibrated values for S of all the rows of detector cells are used in the subsequent image reconstruction process.

The Optimization Process

In optimizing the objective function (2) via the nonlinear least square fitting algorithm, an initial set of parameters is firstly used. This initial set of parameters is a set of parameters expressed by a vector $V_{ini}$, including the following parameters: position parameters of the calibration phantom (x, y); and a set of unknown geometric parameters (S); where the set of unknown geometric parameters (S) includes modGap indicative of the size of the air gap between adjacent modules, and colOffset indicative of the ISO channel offset.

It should be understood that the set of unknown geometric parameters is not limited to the geometric parameters listed above. Appropriate geometric parameters could be selected by a skilled artisan upon actual needs.

The initial values of the position parameters x, y of the calibration phantom can be empirically set, while the initial values of the set of unknown geometric parameters (5) may be set according to the designed values of the detector. In one embodiment according to the present invention, the initial values of the position parameters x, y of the calibration phantom can be set to (0, 200), i.e., the calibration phantom is on the y-axis, 200 mm away from the ISO, while modGap has an initial value of 0.15 mm and colOffset has an initial value of 0.

As previously described, in optimizing the objective function (2) via the nonlinear least square fitting algorithm, an initial set of parameters is firstly used, for example, $V_{ini}=(x_0, y_0, S_0)$, where $x_0$, $y_0$ represent initial values of the positions x, y of the calibration phantom, and $S_0$ the initial values of the set of unknown geometric parameters (5). As such, following the forward projection process as described by Equation (1), the calculated projection coordinate of the calibration phantom on the current row of detector cells and corresponding to the angle β can be obtained:

$$x_{p\beta}=P_\beta(x_0,y_0,S_0).$$

For purpose of optimization, the CT scanner needs to perform an axial scan of the calibration phantom in the SFOV for a plurality of angles so as to obtain projection images for corresponding angles. Then, projection data corresponding to the current row of detector cells are extracted from the obtained projection images corresponding to the plurality of angles, and the Gaussian center of the projection data of the calibration phantom on the current row of detector cells and corresponding to each angle is calculated, which serves as the actual projection coordinate of the calibration phantom on the current row of detector cells and corresponding to that angle. Following Equation (1), the calculated projection coordinate of the calibration phantom on the current row of detector cells and corresponding to each angle is obtained. Then, a final set of parameters (V) is obtained via the nonlinear least square fitting algorithm, based on the actual projection coordinates for the plurality of angles and the corresponding calculated projection coordinates. The values of S in the final set of parameters (V) are closest to the corresponding actual values.

Figure 5:
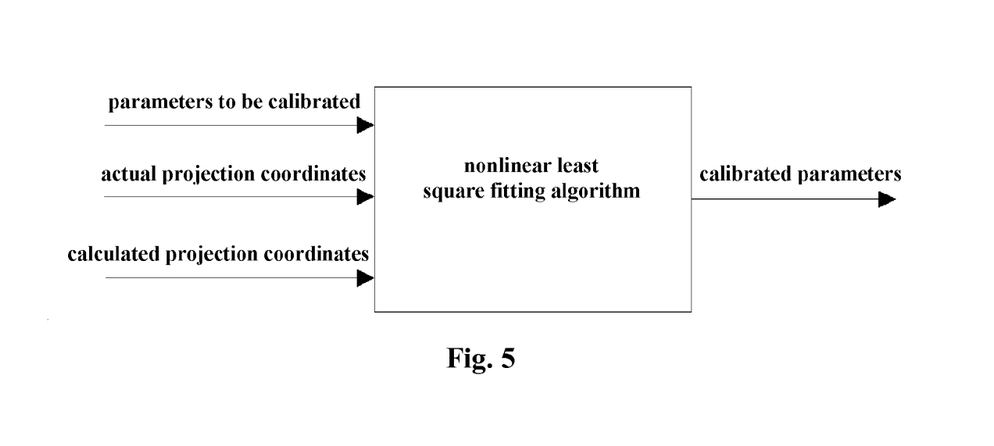
FIG. 5 schematically shows the input and output of the nonlinear least square fitting algorithm according to one embodiment of the present invention.

FIG. 5 schematically shows the input and output of the nonlinear least square fitting algorithm according to one embodiment of the present invention. Parameters to be calibrated, actual projection coordinates and calculated projection coordinates of the calibration phantom on the current row of detector cells and corresponding to a plurality of angles, may be inputted into the nonlinear least square fitting algorithm, so as to obtain geometric parameters that best match the installed CT scanner. As shown in FIG. 5, parameters to be calibrated, actual projection coordinates and calculated projection coordinates of the calibration phantom on the current row of detector cells and corresponding to a plurality of angles serve as the input for the nonlinear least square fitting algorithm, via which the parameters to be calibrated are optimized to produce calibrated parameters.

When performing an independent geometric calibration on a certain row of detector cells (having a structure of 5×4×34), parameters to be calibrated, actual and calculated projection coordinates of the calibration phantom on the current row of detector cells and corresponding to at least 7 angles, serve as the input for the nonlinear least square fitting algorithm, via which the parameters to be calibrated are optimized to produce calibrated parameters. According to one embodiment of the present invention, parameters to be calibrated, actual and calculated projection coordinates of the calibration phantom on the current row of detector cells and corresponding to 984 angles serve as the input for the nonlinear least square fitting algorithm, via which the parameters to be calibrated are optimized to produce calibrated parameters.

In accordance with one embodiment of the present invention, parameters to be calibrated may be optimized via, for example, the Powell optimization algorithm, or any other appropriate nonlinear least square fitting algorithm.

Thus, calibrated geometric parameters will be utilized in clinical applications to obtain a high quality reconstructed image, wherein ring artifacts are eliminated, and the MTF is improved.

Figure 6:
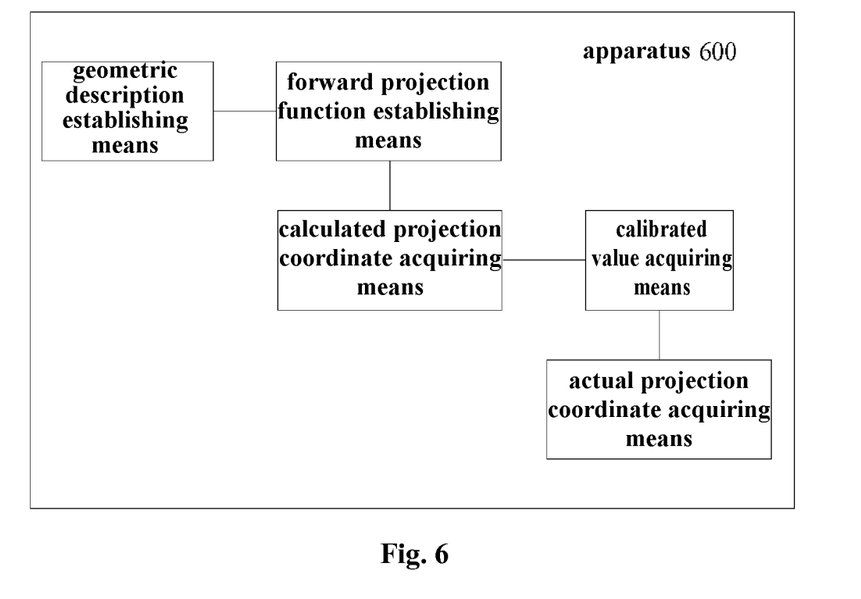
FIG. 6 is a block diagram illustrating an apparatus for geometric calibration of a CT scanner having a large flat module detector according to one embodiment of the present invention.

FIG. 6 is a block diagram illustrating an apparatus 600 for geometric calibration of a CT scanner having a large flat module detector according to one embodiment of the present invention. The apparatus 600 includes: a geometric description establishing means for establishing a complete geometric description of the CT scanner, said complete geometric description including at least one unknown geometric parameter; a forward projection function establishing means for establishing a description of a forward projection function using said complete geometric description; an actual projection coordinate acquiring means for acquiring actual projection coordinates of a calibration phantom placed in a scanning field of view (SFOV) on a current row of detector cells and corresponding to a plurality of angles; a calculated projection coordinate acquiring means for acquiring calculated projection coordinates of the calibration phantom on the current row of detector cells and corresponding to the plurality of angles using the description of said forward projection function; and a calibrated value acquiring means for acquiring a calibrated value for said at least one unknown geometric parameter by evaluating said at least one unknown geometric parameter based on the acquired actual projection coordinates and calculated projection coordinates via a nonlinear least square fitting algorithm.

Table 2 shows calibrated values and simulation values based on digital simulation after geometric calibration according to an embodiment of the present invention.

TABLE 2

| | Items | ISO channel Offset (the number of channels) | Air gap 1 between adjacent modules (mm) | Air gap 2 between adjacent modules (mm) | Air gap 3 between adjacent modules (mm) | Air gap 4 between adjacent modules (mm) |
|---|---|---|---|---|---|---|
| Group 1 | Simulation value | −5.272 | 0.08 | 0.24 | 0.30 | 0.18 |
| | Calibrated value | −5.270 | 0.075 | 0.241 | 0.299 | 0.177 |
| Group 2 | Simulation value | −5.25 | 0.28 | 0.56 | 0.48 | 0.38 |
| | Calibrated value | −5.248 | 0.272 | 0.559 | 0.480 | 0.372 |

As seen from the calibrated values and simulation values listed in Table 2, the calibrated geometric parameters (i.e., the calibrated values) resulted from geometric calibration according to one embodiment of the present invention are almost equal to the geometric parameters (i.e., the simulation values) given in the simulation.

Figure 7:
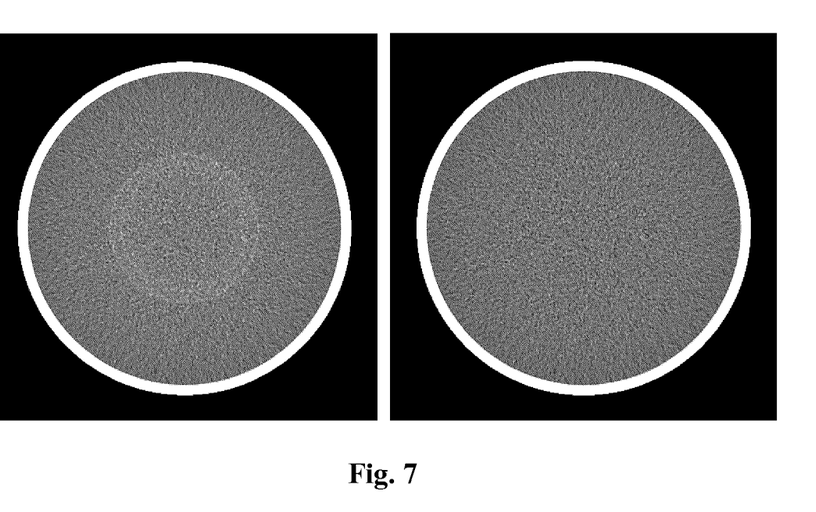
FIG. 7 provides a contrast of a reconstructed image before and after geometric calibration according to one embodiment of the present invention on the basis of digital simulation.

FIG. 7 provides a contrast of a reconstructed image before and after geometric calibration according to one embodiment of the present invention on the basis of digital simulation. On the left is a reconstructed image before geometric calibration, wherein a ring artifact appears, and on the right is a reconstructed image after geometric calibration, wherein the ring artifact has been eliminated.

Figure 8:
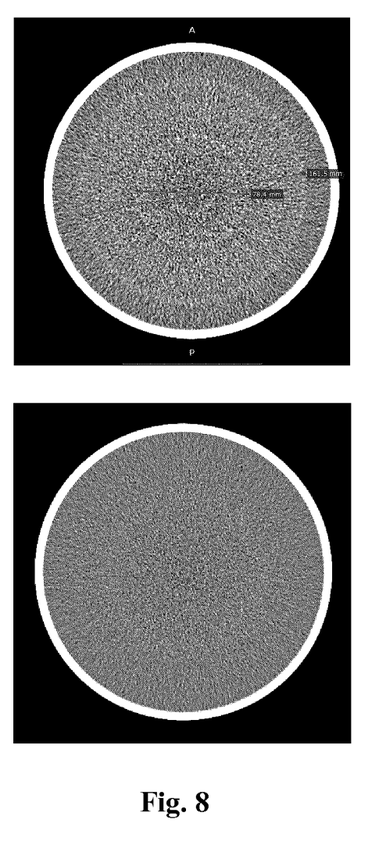
FIG. 8 provides a contrast of a water phantom reconstructed image before and after geometric calibration according to one embodiment of the present invention based on real data from a CT scanner having a large flat module detector.

FIG. 8 provides a contrast of a water phantom reconstructed image before and after geometric calibration according to one embodiment of the present invention based on real data from a CT scanner having a large flat module detector. The upper drawing shows a water phantom reconstructed image before geometric calibration, wherein two ring artifacts appear. The outer ring artifact having a diameter of 161.5 mm while the inner ring artifact having a diameter of 78.4 mm. The lower drawing is a water phantom reconstructed image after geometric calibration, wherein the ring artifacts are eliminated.

Figure 9:
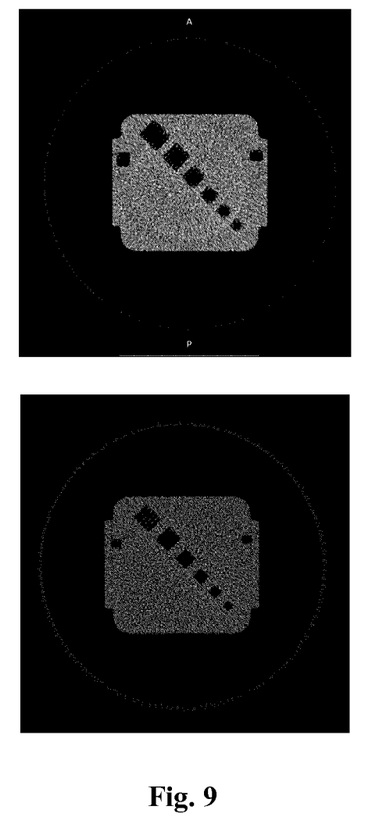
FIG. 9 provides a contrast of a QA phantom reconstructed image before and after geometric calibration according to one embodiment of the present invention based on real data from a CT scanner having a large flat module detector.

FIG. 9 provides a contrast of a QA phantom reconstructed image before and after geometric calibration according to one embodiment of the present invention based on real data from a CT scanner having a large flat module detector. The upper drawing shows a QA phantom reconstructed image before geometric calibration, and the lower drawing is a QA phantom reconstructed image after geometric calibration. As is seen, after geometric calibration according to one embodiment of the present invention, the resolution of the QA phantom reconstructed image is improved.

Figure 10:
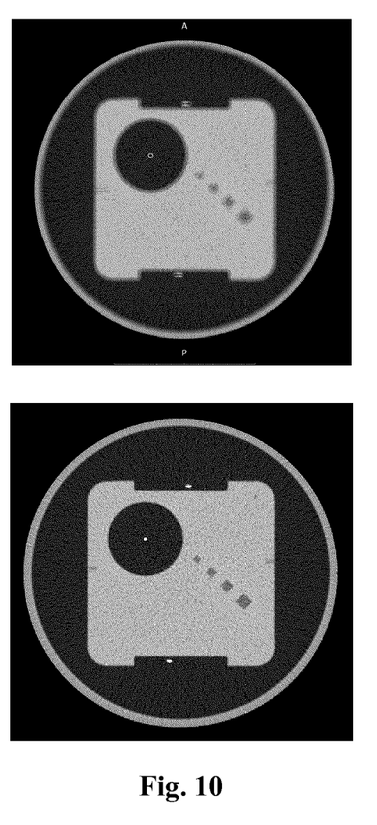
FIG. 10 provides a contrast of a GEPP phantom reconstructed image before and after geometric calibration according to one embodiment of the present invention based on real data from a CT scanner having a large flat module detector.

FIG. 10 provides a contrast of a GEPP phantom reconstructed image before and after geometric calibration according to one embodiment of the present invention based on real data from a CT scanner having a large flat module detector. The upper drawing shows a GEPP phantom reconstructed image before geometric calibration, and the lower drawing is a GEPP phantom reconstructed image after geometric calibration. As is seen, after geometric calibration according to one embodiment of the present invention, double shadow artifacts incurred by the inaccurate ISO channel are eliminated, which leads to the improved MTF.

The method and apparatus according to the present invention can perform an easy and fast geometric calibration of a CT scanner having a large flat module detector via a very simple calibration phantom (e.g., a pin), and the introduction of a pin will not significantly increase the cost. The present invention only resorts to an ordinary axial scan and thus can easily be extended to products in the future. In addition, since the present invention utilizes a nonlinear least square fitting algorithm for parameter optimization, the calculation is very fast and reliable, and can typically be completed in 2-3 seconds.

While the present invention has been described in detail with reference to specific embodiments, a skilled person will understand that the present invention is not limited to said embodiments. Many modifications and variations may be made to the present invention without departing from the scope of the present invention that is defined in the appending claims.

What is claimed is:

1. A method for geometric calibration of a CT scanner having at least one row of detector cells, the method comprising:

executing the following for each row of the at least one row of detector cells:
   establishing a complete geometric description of the CT scanner, wherein the complete geometric description comprises at least one unknown geometric parameter;
   establishing a description of a forward projection function using the complete geometric description;
   acquiring actual projection coordinates of a calibration phantom placed in a scanning field of view (SFOV) on a current row of detector cells and corresponding to a plurality of angles, wherein the current row of detector cells has a structure of n×q×r, where n denotes the number of modules, q denotes the number of packs in each module, and r denotes the number of detector cells in each pack and the at least one unknown geometric parameter comprises sizes of (n−1) air gaps between adjacent modules, and an ISO channel offset;
   acquiring calculated projection coordinates of the calibration phantom on the current row of detector cells and corresponding to the plurality of angles using the description of the forward projection function; and
   acquiring a calibrated value for the at least one unknown geometric parameter by evaluating said at least one unknown geometric parameter based on the acquired actual projection coordinates and calculated projection coordinates using a nonlinear least square fitting algorithm.

2. The method according to claim 1, wherein the forward projection function is described as follows:

$$x_{p_\beta} = P_\beta(x,y,S),$$

wherein $x_{p_\beta}$ denotes a calculated projection coordinate of the calibration phantom on the current row of detector cells and corresponding to a forward projection angle $\beta$, x and y are coordinates of the calibration phantom, S is a set comprising the at least one unknown geometric parameter, and P is a description of the forward projection function.

3. The method according to claim 2, wherein acquiring a calibrated value further comprises minimizing the following objective function by evaluating the at least one unknown geometric parameter using the nonlinear least square fitting algorithm:

$$F = \Sigma_{i=1}^{m}(x'_p(\beta_i) - P_{\beta_i}(x,y,S))^2,$$

wherein F denotes the objective function, $\beta_i$ denotes a current scan angle, m represents the number of scan angles, $x'_p(\beta_i)$ represents an actual projection coordinate of the calibration phantom on the current row of detector cells and corresponding to the current scan angle, and $P_{\beta_i}(x, y, S)$ denotes a calculated projection coordinate of the calibration phantom on the current row of detector cells and corresponding to the current scan angle.

4. The method according to claim 3, wherein the actual projection coordinate of the calibration phantom on the current row of detector cells and corresponding to the current scan angle is the Gaussian center of projection data of the calibration phantom on the current row of detector cells and corresponding to the current scan angle.

5. The method according to claim 1, wherein the actual projection coordinates of the calibration phantom on the current row of detector cells and corresponding to the plurality of angles are obtained by an axial scan of the calibration phantom for the plurality of angles.

6. The method according to claim 1, wherein the nonlinear least square fitting algorithm includes the Powell optimization algorithm.

7. The method according to claim 1, wherein the calibration phantom is a pin having a length of 100 mm and a diameter of 2 mm.

8. The method according to claim 1, wherein the calibrated value for the at least one unknown geometric parameter is used for subsequent image reconstruction.

9. An apparatus for geometric calibration of a CT scanner having at least one row of detector cells, the apparatus comprising:

a geometric description establishing device configured to establish a complete geometric description of the CT scanner, the complete geometric description comprising at least one unknown geometric parameter;
   a forward projection function establishing device configured to establish a description of a forward projection function using the complete geometric description;
   an actual projection coordinate acquiring device configured to acquire actual projection coordinates of a calibration phantom placed in a scanning field of view (SFOV) on a current row of detector cells and corresponding to a plurality of angles, wherein the current row of detector cells has a structure of n×q×r, where n denotes the number of modules, q denotes the number of packs in each module, and r denotes the number of detector cells in each pack and the at least one unknown geometric parameter comprises sizes of (n−1) air gaps between adjacent modules, and an ISO channel offset;
   a calculated projection coordinate acquiring device configured to acquire calculated projection coordinates of the calibration phantom on the current row of detector cells and corresponding to the plurality of angles using the description of the forward projection function; and
   a calibrated value acquiring device configured for acquire a calibrated value for the at least one unknown geometric parameter by evaluating the at least one unknown geometric parameter based on the acquired actual projection coordinates and calculated projection coordinates via a nonlinear least square fitting algorithm.

10. The apparatus according to claim 9, wherein the forward projection function is described as follows:

$$x_{p_\beta} = P_\beta(x, y, S),$$

wherein $x_{p_\beta}$ denotes a calculated projection coordinate of the calibration phantom on the current row of detector cells and corresponding to a forward projection angle $\beta$, x and y are coordinates of the calibration phantom, S is a set comprising the at least one unknown geometric parameter, and P is a description of the forward projection function.

11. The apparatus according to claim 10, wherein the calibrated value acquiring device comprises an objective function minimizing part configured to minimize the following objective function by evaluating said at least one unknown geometric parameter via said nonlinear least square fitting algorithm:

$$F = \Sigma_{i=1}^{m}(x'_p(\beta_i) - P_{\beta_i}(x, y, S))^2,$$

wherein F denotes the objective function, $\beta_i$ denotes a current scan angle, m represents the number of scan angles, $x'_p(\beta_i)$ represents an actual projection coordinate of the calibration phantom on the current row of detector cells and corresponding to the current scan angle, and $P_{\beta_i}(x, y, S)$ denotes a calculated projection coordinate of the calibration phantom on the current row of detector cells and corresponding to the current scan angle.

12. The apparatus according to claim 11, wherein the actual projection coordinate of the calibration phantom on the current row of detector cells and corresponding to the current scan angle is the Gaussian center of projection data of the calibration phantom on the current row of detector cells and corresponding to the current scan angle.

13. The apparatus according to claim 9, wherein the actual projection coordinates of the calibration phantom on the current row of detector cells and corresponding to the plurality of angles are obtained by an axial scan of the calibration phantom for the plurality of angles.

14. The apparatus according to claim 9, wherein the nonlinear least square fitting algorithm includes the Powell optimization algorithm.

15. The apparatus according to claim 9, wherein the calibrated value for the at least one unknown geometric parameter is used for subsequent image reconstruction.

16. A CT scan system, comprising: an apparatus for geometric calibration of a CT scanner having at least one row of detector cells the apparatus comprising:
a geometric description establishing device configured to establish a complete geometric description of the CT scanner, the complete geometric description comprising at least one unknown geometric parameter;
a forward projection function establishing device configured to establish a description of a forward projection function using the complete geometric description;
an actual projection coordinate acquiring device configured to acquire actual projection coordinates of a calibration phantom placed in a scanning field of view (SFOV) on a current row of detector cells and corresponding to a plurality of angles, wherein the current row of detector cells has a structure of n×q×r, where n denotes the number of modules, q denotes the number of packs in each module, and r denotes the number of detector cells in each pack and the at least one unknown geometric parameter comprises sizes of (n−1) air gaps between adjacent modules, and an ISO channel offset;
a calculated projection coordinate acquiring device configured to acquire calculated projection coordinates of the calibration phantom on the current row of detector cells and corresponding to the plurality of angles using the description of the forward projection function; and
a calibrated value acquiring device configured for acquire a calibrated value for the at least one unknown geometric parameter by evaluating the at least one unknown geometric parameter based on the acquired actual projection coordinates and calculated projection coordinates via a nonlinear least square fitting algorithm.

* * * * *